United States Patent
Kaneko

(10) Patent No.: US 7,459,551 B2
(45) Date of Patent: Dec. 2, 2008

(54) METHOD FOR PREPARING CYCLIC COMPOUNDS

(75) Inventor: Akira Kaneko, Niigata (JP)

(73) Assignee: Asubio Pharma Co., Ltd., Tokyo (JP)

( * ) Notice: Subject to any disclaimer, the term of this patent is extended or adjusted under 35 U.S.C. 154(b) by 365 days.

(21) Appl. No.: 10/508,659

(22) PCT Filed: Mar. 26, 2003

(86) PCT No.: PCT/JP03/03737

§ 371 (c)(1),
(2), (4) Date: May 25, 2005

(87) PCT Pub. No.: WO03/080543

PCT Pub. Date: Oct. 2, 2003

(65) Prior Publication Data

US 2005/0209450 A1    Sep. 22, 2005

(30) Foreign Application Priority Data

Mar. 26, 2002  (JP)  ............... 2002-086575

(51) Int. Cl.
| | | |
|---|---|---|
| C07D 499/00 | (2006.01) | |
| C07D 487/00 | (2006.01) | |
| C07D 487/08 | (2006.01) | |
| C07D 501/00 | (2006.01) | |
| C07D 221/00 | (2006.01) | |
| C07D 237/00 | (2006.01) | |
| C07D 239/00 | (2006.01) | |
| C07D 241/00 | (2006.01) | |
| C07D 251/00 | (2006.01) | |
| C07D 253/00 | (2006.01) | |
| C07D 255/00 | (2006.01) | |
| C07D 257/00 | (2006.01) | |
| C07D 259/00 | (2006.01) | |
| C07D 205/00 | (2006.01) | |

(52) U.S. Cl. ............... 540/310; 540/201; 540/205; 540/215; 540/302; 540/347

(58) Field of Classification Search ............... None
See application file for complete search history.

(56) References Cited

FOREIGN PATENT DOCUMENTS

| EP | 212404 A1 | 3/1987 |
| EP | 272747 A1 | 7/1988 |
| EP | 0 399 228 A | 11/1990 |
| EP | 597401 A2 | 5/1994 |
| JP | 6422880 | 1/1989 |
| JP | 06 072875 | 3/1994 |
| WO | WO 93 03042 | 2/1993 |

OTHER PUBLICATIONS

Battistini et al. "A New Route To Penems And Carbapenems" Tetrahedron Letters, vol. 25, No. 22, 1984, pp. 2395-2398.
Perrone et al. "The Carbonyl-Carbonyl Coupling Route To Penems: A Stepwise Analysis" Tetrahedron Letters, vol. 25, No. 22, 1984, pp. 2399-2402.
Budt et al. "Alkylphosphonous Acid Diesters Novel Reagent For The Oxalimide Cyclisation To Penems" Tetrahedron Letters, vol. 33, No. 37, 1992, pp. 5331-5334.

*Primary Examiner*—Shaojia Anna Jiang
*Assistant Examiner*—Layla Bland
(74) *Attorney, Agent, or Firm*—Paul E. White; Manelli Denison & Selter PLLC

(57) ABSTRACT

The present invention provides a method for preparing a β-lactam compound of the following Formula (3), which comprises the step of reacting a compound of the following Formula (1) with a trialkyl phosphite represented by the formula $(R^5O)_3P$ (wherein $R^5$ represents an ethyl group, etc.) in an amount of 2 to 5 moles per mole of the compound and the step of heating the resulting reaction mixture in a diluent, wherein said method is characterized by having the step of completely removing unreacted trialkyl phosphite from the reaction mixture prior to the step of heating.

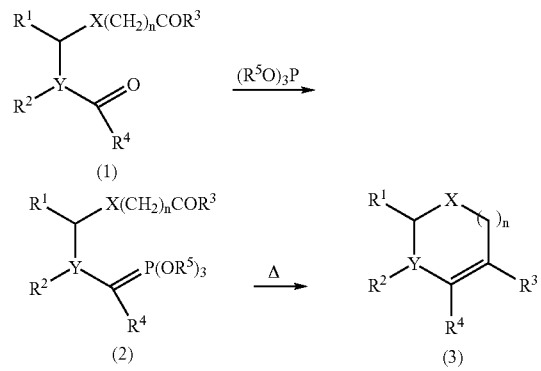

(wherein X represents S, etc., Y represents N, etc., n represents 0 or 1, $R^1$ represents an optionally substituted alkyl group containing 1 to 10 carbon atoms, etc., $R^2$ and $R^3$ each represent an optionally substituted alkyl or heterocyclic group, etc., and $R^4$ represents an alkenyloxy group containing 1 to 6 carbon atoms, etc., provided that $R^1$ and $R^2$ may together form a β-lactam ring, etc.)

2 Claims, No Drawings

METHOD FOR PREPARING CYCLIC COMPOUNDS

This application is the national phase of international application PCT/JP03/03737 filed Mar. 26, 2003 which designated the U.S.

TECHNICAL FIELD

The present invention relates to an industrially advantageous method for preparing a compound having a cyclic structure in its molecule (hereinafter referred to as a "cyclic compound"), which is useful, e.g., as a starting material for the production of pharmaceuticals, agrochemicals, etc. More specifically, the present invention relates to a method for preparing a cyclic compound, which comprises the step of forming a cyclic structure through intramolecular cyclization using a trialkyl phosphate.

BACKGROUND ART

As for the preparation of cyclic compounds such as a penem derivative of Formula (8), for example, the method shown in the following reaction scheme has been conventionally known (see, e.g., JP 63-162694 A and JP 6-72875 A):

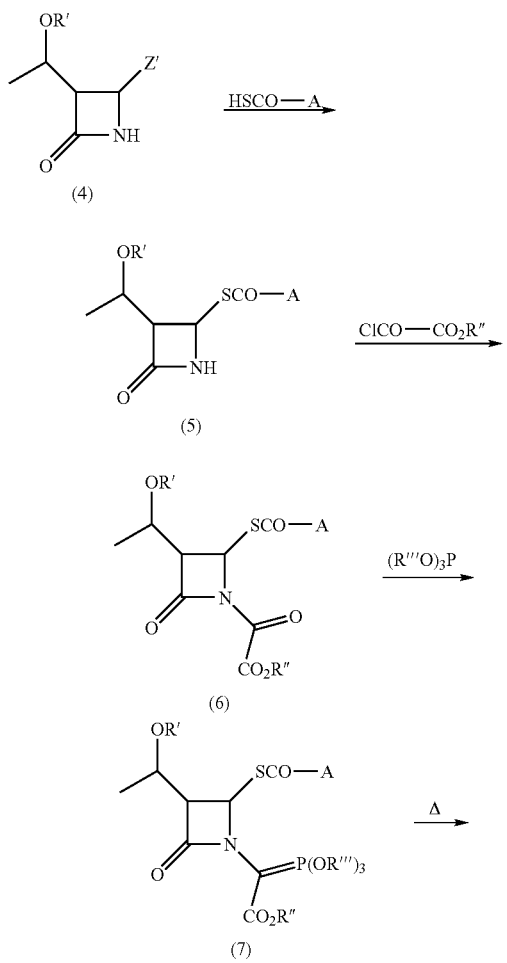

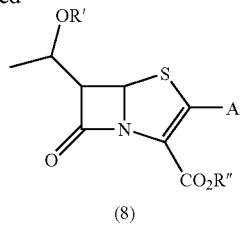

(wherein R' represents a t-butyldimethylsilyl group or the like, Z' represents an acetoxy group or the like, A represents a 5- or 6-membered heteroaliphatic group containing 1 or 2 ring oxygen atoms or the like, R" represents an allyl group or the like, and R'" represents an ethyl group or the like).

In the above reaction scheme, however, the step of obtaining a phosphorus ylide compound of Formula (7) from a compound of Formula (6) is actually accomplished by using an excess amount (more than two-fold molar excess) of a trialkyl phosphate represented by the formula $(R'''O)_3P$ to react with the compound of Formula (6) for the purpose of improving the reaction yield. Moreover, the reaction mixture is purified using the technique of flash column chromatography before being provided for cyclization to obtain a compound of Formula (8).

However, such technique of flash column chromatography is cumbersome to use when these reactions are performed on an industrial scale, and is also unfavorable in terms of work efficiency. In addition, when the unpurified reaction mixture is directly provided for cyclization, a target product could not be obtained in high yield because structurally unidentified impurities would be by-produced with the target product.

Since the above compound of Formula (8) has more than one asymmetric carbon atom in its molecule and often requires expensive reactants, it is important to obtain a target product in higher yield for its industrially advantageous preparation. Thus, there has been a demand for the development of an industrially advantageous method to prepare a cyclic compound through intramolecular cyclization of a phosphorus ylide compound obtained using a trialkyl phosphite.

DISCLOSURE OF THE INVENTION

The present invention has been made by taking into consideration the above situation, and aims to provide an industrially advantageous method for preparing a cyclic compound using a trialkyl phosphite through intramolecular cyclization.

As a result of detailed investigations made to determine the cause of reduced yield in the above cyclization step, the inventors of the present invention have found that the yield of cyclization is reduced when unreacted trialkyl phosphite is not sufficiently removed from the reaction mixture obtained after reaction with an excess amount of trialkyl phosphite and hence the trialkyl phosphite, even in a little amount, still remains in the reaction mixture. In turn, they have found that the yield is significantly improved when cyclization is performed after removal of trialkyl phosphate from the reaction mixture. These findings led to the completion of the present invention.

According to the first aspect of the present invention, a method is provided for preparing a cyclic compound of Formula (3):

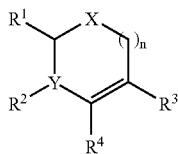

(wherein X represents $CH_2$, O or S, Y represents CH or N, n represents 0 or 1, $R^1$ represents an optionally substituted alkyl group containing 1 to 10 carbon atoms, $R^2$ and $R^3$ each independently represent an optionally substituted alkyl group containing 1 to 6 carbon atoms, an optionally substituted alkenyl group containing 1 to 6 carbon atoms, an optionally substituted phenyl group, an optionally substituted heterocyclic group or an optionally substituted heteroylmethyl group, and $R^4$ represents an alkoxycarbonyl group containing 1 to 6 carbon atoms, a haloalkoxycarbonyl group containing 1 to 6 carbon atoms or an alkenyloxycarbonyl group containing 1 to 6 carbon atoms, provided that $R^1$ and $R^2$ may together form a carbocyclic ring containing 3 to 8 carbon atoms or a heterocyclic ring containing 2 to 7 carbon atoms), which comprises:

the step of reacting a compound of Formula (1):

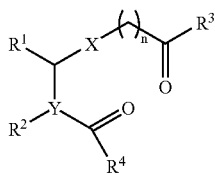

(wherein X, Y, n, $R^1$, $R^2$, $R^3$ and $R^4$ are as defined above) with a trialkyl phosphate represented by the formula $(R^5O)_3P$ (wherein $R^5$ represents an alkyl group containing 1 to 4 carbon atoms) in an amount of 2 to 5 moles per mole of the compound to obtain a reaction mixture containing a compound of Formula (2):

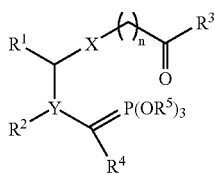

(wherein X, Y, n, $R^1$, $R^2$, $R^3$, $R^4$ and $R^5$ are as defined above); and the step of heating the resulting mixture in a diluent, wherein said method is characterized by having the step of removing unreacted trialkyl phosphate from the reaction mixture prior to the step of heating the reaction mixture in a diluent.

In the method of the present invention, the step of removing unreacted trialkyl phosphate from the reaction mixture preferably comprises reducing the internal pressure of the vessel holding the above reaction mixture to 0.7 kPa or below and heating the vessel at 75° C. to 80° C. to distill off the trialkyl phosphite remaining in the above reaction mixture.

In the method of the present invention, the step of removing unreacted trialkyl phosphate from the reaction mixture more preferably comprises reducing the internal pressure of the vessel holding the above reaction mixture to 0.7 to 2 kPa and heating the vessel at 50° C. to 75° C. to distill off low-boiling products, followed by reducing the internal pressure of the vessel to 0.7 kPa or below and heating at 75° C. to 80° C. to distill off the trialkyl phosphite remaining in the above reaction mixture.

In particular, the method of the present invention is preferably applicable to the preparation of a cyclic compound of Formula (3) which has a β-lactam ring in its molecule.

Namely, a preferred embodiment of the present invention is directed to a method for preparing a β-lactam compound of Formula (3-1):

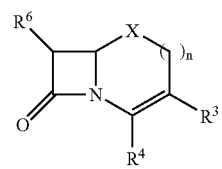

(wherein X, n, $R^3$ and $R^4$ are as defined above and $R^6$ represents a hydroxyalkyl group whose hydroxy moiety is protected with a protecting group), which comprises:

the step of reacting a compound of Formula (1-1):

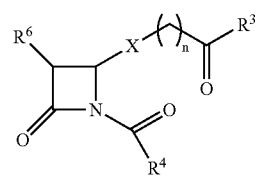

(wherein X, n, $R^3$, $R^4$ and $R^6$ are as defined above) with a trialkyl phosphite represented by the formula $(R^5O)_3P$ (wherein $R^5$ represents an alkyl group containing 1 to 4 carbon atoms) in an amount of 2 to 5 moles per mole of the compound to obtain a reaction mixture containing a compound of Formula (2-1):

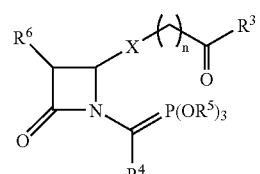

(wherein X, n , $R^3$, $R^4$, $R^5$ and $R^6$ are as defined above); and the step of heating the resulting mixture in a diluent, wherein said method is characterized by having the step of removing unreacted trialkyl phosphate from the reaction mixture prior to the step of heating the reaction mixture in a diluent.

BEST MODE FOR CARRYING OUT THE INVENTION

The method of the present invention has the following steps: (A) reacting a compound of Formula (1) with an excess amount of a trialkyl phosphate to obtain a reaction mixture containing a compound of Formula (2); (B) removing unreacted trialkyl phosphite from the reaction mixture; and (C) heating the reaction mixture in the presence of a diluent.

The method of the present invention is illustrated by the following reaction scheme.

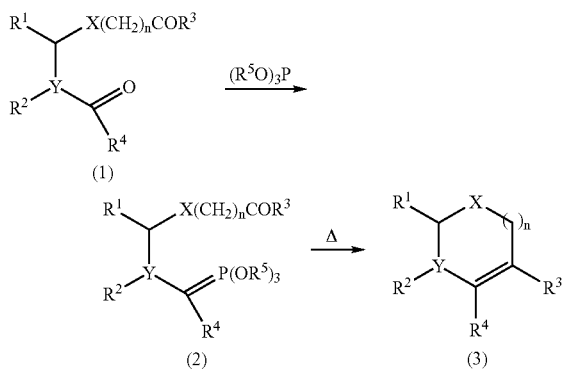

I) Step of Obtaining a Reaction Mixture Containing a Compound of Formula (2)

As a first step, a compound of Formula (1) is reacted with a trialkyl phosphite represented by the formula $(R^5O)_3P$ to give a compound of Formula (2).

In Formula (1), X represents $CH_2$, O or S, with S being particularly preferred.

n represents 0 or 1, with 0 being particularly preferred.

$R^1$ represents an optionally substituted alkyl group containing 1 to 10 carbon atoms.

Examples of an alkyl group containing 1 to 10 carbon atoms defined for $R^1$ include, for example, a methyl group, an ethyl group, a n-propyl group, an isopropyl group, a n-butyl group, a sec-butyl group, an isobutyl group, a t-butyl group, a n-pentyl group, a neopentyl group, a n-hexyl group, an isohexyl group, a n-heptyl group, a n-octyl group and a n-decyl group.

Examples of a substituent include a hydroxy group; a cyano group; a nitro group; an alkoxy group such as a methoxy group, an ethoxy group, a n-propoxy group, an isopropoxy group, a n-butoxy group or a t-butoxy group; a trialkylsilyloxy group such as a trimethylsilyloxy group, a t-butyldimethylsilyloxy group or a triethylsilyloxy group; a triarylsilyloxy group such as a triphenylsilyloxy group; an alkoxycarbonyloxy group such as a t-butoxycarbonyloxy group; an alkoxyalkoxy group such as a methoxymethoxy group or a 1-ethoxyethoxy group; an alkylthio group such as a methylthio group, an ethylthio group, a n-propylthio group or a butylthio group; an alkoxycarbonyl group such as a methoxycarbonyl group or an ethoxycarbonyl group; an optionally substituted phenyl group such as a phenyl group, a 4-chlorophenyl group or a 3-methoxyphenyl group; an optionally substituted amino group such as an amino group, an acetylamino group, a methylamino group, a phenylamino group or a dimethylamino group; an optionally substituted aminocarbonyl group such as an amide group, an N-methylaminocarbonyl group or an N,N-dimethylaminocarbonyl group; a 2-tetrahydropyranyloxy group; and a 1,3-dioxan-2-yl group. These substituents may be attached to any carbon atom in the alkyl group containing 1 to 10 carbon atoms. Also, one or more substituents, which may be the same or different, may be attached to the alkyl group.

$R^2$ and $R^3$ each independently represent an alkyl group containing 1 to 6 carbon atoms, such as a methyl group, an ethyl group, a n-propyl group, a n-butyl group, an isopropyl group, a sec-butyl group, a t-butyl group, a n-pentyl group or a n-hexyl group; an alkenyl group containing 1 to 6 carbon atoms, such as a vinyl group, a 1-propenyl group, a 2-propenyl group, a 1-butenyl group, a 2-butenyl group, a 2-pentenyl group or a 2-hexenyl group; an optionally substituted phenyl group; an optionally substituted heterocyclic group; or an optionally substituted heteroylmethyl group.

Examples of a heterocyclic ring in the above heterocyclic or heteroylmethyl group include 5- or 6-membered saturated or unsaturated heterocyclic rings containing 1 to 3 oxygen atoms, nitrogen atoms or sulfur atoms as ring member(s).

Examples of a substituent attached to the above phenyl, heterocyclic or heteroylmethyl group include, for example, a halogen atom such as fluorine or chlorine; an alkyl group such as a methyl group or an ethyl group; an alkoxy group such as a methoxy group or an ethoxy group; a dialkylamino group such as a dimethylamino group; a cyano group; and a nitro group. One or more of these substituents, which may be the same or different, may be substituted on any position of the benzene or heterocyclic ring.

Among those listed above, preferred as $R^3$ is, for example, a saturated or unsaturated heterocyclic group containing one ring oxygen atom (e.g., tetrahydrofuran, tetrahydropyran, furan, pyran) or a saturated or unsaturated heterocyclic group containing two ring oxygen atoms (e.g., 1,3-dioxolane, 1,4-dioxane, 1,3-dioxane). More preferred is a 5- or 6-membered saturated heterocyclic group containing one or two ring oxygen atoms.

Heterocyclic groups particularly preferred as $R^3$ include saturated 5- or 6-membered heterocyclic groups containing one ring oxygen atom, as exemplified by tetrahydrofuran-2-yl, tetrahydrofuran-3-yl, tetrahydropyran-2-yl, 1,3-dioxolan-2-yl, 1,4-dioxan-2-yl, 1,3-dioxan-2-yl, tetrahydropyran-3-yl and tetrahydropyran-4-yl.

$R^4$ represents an alkoxycarbonyl group containing 1 to 6 carbon atoms, such as a methoxycarbonyl group, an ethoxycarbonyl group, a n-propoxycarbonyl group, an isopropoxycarbonyl group, a n-butoxycarbonyl group, a sec-butoxycarbonyl group, a t-butoxycarbonyl group or a n-pentyloxycarbonyl group; a haloalkoxycarbonyl group containing 1 to 6 carbon atoms, such as a 2,2,2-trichloroethoxycarbonyl group; or an alkenyloxycarbonyl group containing 1 to 6 carbon atoms, such as a vinyloxycarbonyl group, a 1-propenyloxycarbonyl group, a 2-propenyloxycarbonyl group, a 1-butenyloxycarbonyl group, a 2-butenyloxycarbonyl group, a 2-pentenyloxycarbonyl group or a 2-hexenyloxycarbonyl group. Among them, a 2-propenyloxycarbonyl group is particularly preferred because it can be hydrolyzed under neutral conditions.

Y represents CH or N, with N being particularly preferred.

Alternatively, $R^1$ and $R^2$ may together form a carbocyclic ring containing 3 to 8 carbon atoms or a heterocyclic ring containing 2 to 7 carbon atoms.

Examples of such a carbocyclic ring containing 3 to 8 carbon atoms include a cyclopropane ring, a cyclobutane ring, a cyclopentane ring, a cyclopentene ring, a cyclohexane ring, a cyclohexene ring, a benzene ring, a cycloheptane ring and a cyclooctane ring.

Examples of such a heterocyclic ring containing 2 to 7 carbon atoms include an aziridine ring, an azetidine ring, a β-lactam ring, a γ-lactam ring, a δ-lactam ring, a pyrrole ring, a pyrrolidine ring and a piperidine ring.

The compound of Formula (1) has optical isomers and stereoisomers based on its asymmetric carbon atom(s), all of which are intended to fall within the scope of the present invention. Moreover, all the reactions involved in the method of the present invention are intended to proceed without any configuration changes, so that racemization does not occur in principle.

Among compounds within the scope of the above Formula (1), a β-lactam compound of the following Formula (1-1):

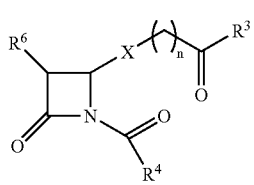

(1-1)

is particularly preferred for use in the method of the present invention.

In the above Formula (1-1), X, n, $R^3$ and $R^4$ are as defined above.

$R^6$ represents a hydroxyalkyl group whose hydroxy moiety is protected with a protecting group.

There is no particular limitation on the protecting group for hydroxy groups as long as it is stable during the reaction in each step of the invented method and is readily deprotected under mild conditions.

Specific examples of the protecting group for hydroxy groups include a trialkylsilyl group, an aryldialkylsilyl group, a diarylalkylsilyl group, a triarylsilyl group, an alkyl group containing 1 to 6 carbon atoms which is substituted with an alkoxy group containing 1 to 6 carbon atoms, a triphenylmethyl group, and a tetrahydropyranyl group.

Specific examples of $R^6$ include a trimethylsilyloxymethyl group, a 1-trimethylsilyloxyethyl group, a 1-trimethylsilyloxypropyl group, a t-butyldimethylsilyloxymethyl group, a 1-t-butyldimethylsilyloxyethyl group, a 1-t-butyldimethylsilyloxypropyl group, a phenyldimethylsilyloxymethyl group, a 1-phenyldimethylsilyloxyethyl group, a 1-phenyldimethylsilyloxyethyl group, a triethylsilyloxymethyl group, a 1-triethylsilyloxyethyl group, a 1-triethylsilyloxypropyl group, a methoxymethyl group, a 1-methoxyethyl group, a 1-methoxypropyl group, a 1-ethoxymethyl group, a 1-ethoxyethyl group, a 1-ethoxypropyl group, a t-butoxymethyl group, a 1-t-butoxyethyl group, a 1-t-butoxypropyl group, a triphenylmethoxymethyl group, a 1-triphenylmethoxyethyl group and a 1-triphenylmethoxypropyl group.

Among those listed above, preferred is a hydroxyalkyl group whose hydroxy moiety is protected with a tri-substituted silyl group because it is readily deprotected under neutral conditions. More preferred is a hydroxyalkyl group whose hydroxy moiety is protected with a t-butyldimethylsilyl group, even more preferred is a 1-(t-butyldimethylsilyloxy)ethyl group, and particularly preferred is a (R)-1-(t-butoxydimethylsilyloxy)ethyl group.

The compound of the above Formula (1-1) has optical isomers based on its asymmetric carbon atoms and stereoisomers, all of which are intended to fall within the scope of the present invention. In the present invention, particularly preferred is a compound that has the S-configuration at the 3-position carbon and the R-configuration at the 4-position carbon of the azetidinone ring.

The compound of the above Formula (1) can be prepared as follows, by way of example.

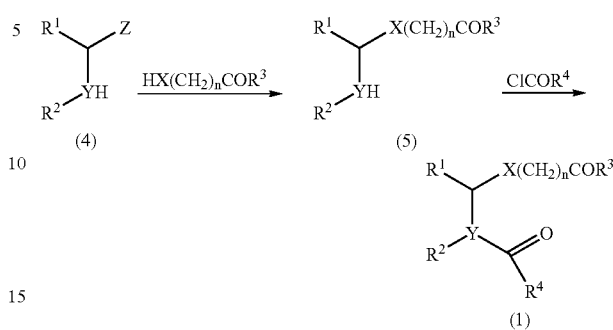

(wherein $R^1$ to $R^4$, X, Y and n are as defined above.)

Namely, the compound of Formula (1) can be obtained by reacting a compound of Formula (4) with a compound of the formula $HX(CH_2)_nC(=O)R^3$ in the presence of a base to give a compound of Formula (5), which is then reacted with an acid chloride of the formula $ClC(=O)R^4$ in the presence of a base.

Examples of a base used in the reactions for obtaining the compounds of Formulae (5) and (1) include metal hydroxides such as sodium hydroxide, potassium hydroxide, magnesium hydroxide and calcium hydroxide; carbonates such as sodium carbonate, potassium carbonate, magnesium carbonate and calcium carbonate; bicarbonates such as sodium bicarbonate and potassium bicarbonate; metal alkoxides such as sodium methoxide, sodium ethoxide, potassium ethoxide, magnesium ethoxide and potassium t-butoxide; and organic bases such as triethylamine, pyridine, lutidine and 1,8-diazabicyclo [5.4.0]undec-7-ene (DBU).

Likewise, examples of a solvent used in the reactions for obtaining the compounds of Formulae (5) and (1) include water; alcohols such as methanol and ethanol; ketones such as acetone and methyl ethyl ketone; ethers such as diethyl ether, tetrahydrofuran and dioxane; halogenated hydrocarbons such as methylene chloride and chloroform; amides such as N,N-dimethylformamide; as well as acetonitrile and dimethyl sulfoxide.

After completion of each reaction, the reaction mixture is extracted with a water-immiscible organic solvent. The organic solvent is washed with water, dried and distilled off to give the compound of Formula (5) or (1).

In a case where the compound of the above Formula (1) is a compound of Formula (1-1), it can be prepared as shown in the following reaction scheme (see JP 63-162694 A), by way of example.

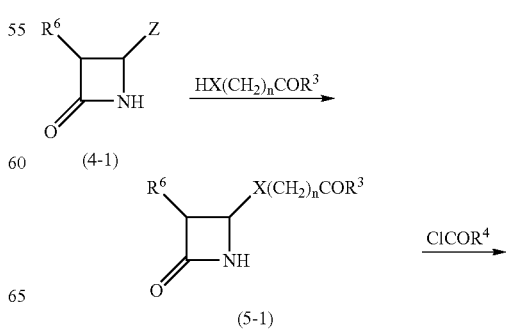

-continued

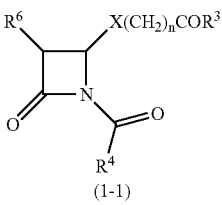

(1-1)

Namely, the compound of Formula (1-1) can be obtained by reacting an azetidinone derivative of Formula (4-1) with a compound of the formula $HX(CH_2)_nC(=O)R^3$ in the presence of a base to give a compound of Formula (5-1), which is then reacted with an acid chloride of the formula $ClC(=O)R^4$ in the presence of a base.

In the above reaction scheme, $R^3$, $R^4$, $R^6$, X and n are as defined above. Z represents a leaving group such as a halogen atom (e.g., fluorine, chlorine, bromine, iodine), an acetoxy group, an arylsulfonyl group (e.g., a phenylsulfonyl group, a 4-methylphenylsulfonyl group) or a (halo)alkylsulfonyl group (e.g., a methylsulfonyl group, an ethylsulfonyl group, a trifluoromethylsulfonyl group).

After completion of each reaction, the reaction mixture is extracted with a water-immiscible organic solvent. The organic solvent is washed with water, dried and distilled off to give the compound of Formula (5) or (1).

The compound of Formula (4), which is used as a starting material, can be prepared as described in JP 61-207373 A, by way of example.

II) Step of Obtaining a Reaction Mixture Containing a Compound of Formula (2)

Next, the compound of Formula (1) is reacted with a trialkyl phosphate represented by the formula $(R^5O)_3P$ to give a compound of Formula (2).

$R^5$ represents an alkyl group containing 1 to 4 carbon atoms, such as methyl, ethyl, n-propyl, isopropyl or n-butyl.

Specific examples of a preferred trialkyl phosphate include trimethyl phosphite, triethyl phosphate, tri-n-propyl phosphate and tri-n-butyl phosphate. Among them, triethyl phosphite is particularly preferred for use in the reaction because a target product will be obtained in high yield, as well as because of its easy availability and being easy to handle, etc.

For this purpose, a commercially available trialkyl phosphite may be used directly or may be purified by distillation or other techniques before use. Alternatively, the trialkyl phosphite used for this purpose may also be prepared in a known manner, for example, by reacting a phosphorus trihalide (e.g., phosphorus trichloride, phosphorus tribromide) with an alcohol represented by the formula $R^5OH$ (wherein $R^5$ is as defined above) in the presence of a tertiary amine or by treating a phosphorus trihalide with an alkoxide represented by the formula $MOR^5$ (wherein M represents an alkali metal or the like and $R^5$ is as defined above).

In this reaction, the trialkyl phosphite is preferably used in an excess amount in terms of obtaining a target product in high yield. The amount of the trialkyl phosphite used in the reaction preferably ranges from 2 to 5 moles, more preferably 4 to 5 moles, per mole of the compound of Formula (1).

Although this reaction may be carried out without using a solvent or in the presence of an appropriate diluent, it is preferable to carry out the reaction without using a solvent because a target product will be obtained with high efficiency and in high yield. Examples of a diluent available for use include, for example, ethers such as tetrahydrofuran and dioxane; aromatic hydrocarbons such as benzene, toluene and xylene; and aliphatic hydrocarbons such as hexane and cyclohexane.

The reaction temperature is 0° C. to 100° C., preferably 20° C. to 80° C. This reaction is exothermic. The reaction time will vary depending on the scale of the reaction, but it is usually several tens of minutes to several hours.

III) Step of Removing Unreacted Trialkyl Phosphite

Next, unreacted trialkyl phosphite is removed from the reaction mixture obtained in Step II) above. Preferably, the trialkyl phosphate is removed completely. If the trialkyl phosphate is not sufficiently removed and hence still remains in the reaction mixture, a target product cannot be obtained in high yield in the subsequent cyclization step.

Procedures used for removal of the trialkyl phosphate are not limited in any way as long as the trialkyl phosphate can be removed from the reaction mixture while ensuring the stable existence (i.e., avoiding the decomposition) of the compound of Formula (2).

A procedure preferably exemplified for removal of the trialkyl phosphate involves reducing the internal pressure of the vessel holding the reaction mixture and heating the vessel at a given temperature to distill off the trialkyl phosphite, a low-boiling product, from the reaction system. In this case, the procedure is preferably performed by stirring the reaction mixture. This procedure allows efficient and almost complete removal of the trialkyl phosphate from the reaction mixture.

The reaction vessel used for the reaction with the trialkyl phosphate can be used continuously to hold the reaction mixture, but another vessel can also be provided for this purpose. In terms of work efficiency, it is preferable to use a reaction vessel capable of reducing pressure therein to ensure a continuous process of obtaining the compound of Formula (2) and removing the trialkyl phosphate.

During removal of the trialkyl phosphate by distillation, both the degree of vacuum and the heating temperature will vary depending on the type of trialkyl phosphate. However, the pressure inside the vessel is usually set to 0.01 to 10 kPa, preferably 0.01 to 5 kPa, while the heating temperature is usually 50° C. to 80° C.

In a case where, for example, triethyl phosphite is used as a trialkyl phosphate, the internal pressure may be set between 0.7 and 2 kPa and the reaction mixture may be heated at 50° C. to 75° C. to remove most part of unreacted triethyl phosphate, followed by heating at 75° C. to 80° C. under a vacuum of 0.7 kPa or below, thus ensuring efficient removal of unreacted triethyl phosphate from the reaction mixture.

The heating time will vary depending on the scale of the reaction, but it is usually several tens of minutes to several hours, preferably 30 to 120 minutes. For complete removal of the trialkyl phosphate, it is preferable to heat the reaction mixture in a vacuum with sufficient stirring.

To confirm whether or not the trialkyl phosphate is removed, for example, a part of the reaction mixture may be sampled and analyzed by a known means such as gas chromatography.

The trialkyl phosphate removed from the reaction mixture can be collected through a condenser connected and attached to the vessel and may be provided again for the reaction after being purified, if necessary.

IV) Step of Obtaining a Compound of Formula (3)

Next, the reaction mixture obtained in Step III) above is dissolved in an appropriate diluent and the resulting solution is heated for cyclization to give a compound of Formula (3).

Although there is no particular limitation on the diluent as long as it is a solvent inert to the reaction, it is preferable to use an organic solvent which ensures homogeneous reaction. Examples of an organic solvent available for use include, for example, halogenated hydrocarbons such as methylene chloride, chloroform, carbon tetrachloride and 1,2-dichloroethane; aromatic hydrocarbons such as benzene, toluene, xylene, chlorobenzene and dichlorobenzene; ethers such as diethyl ether, tetrahydrofuran, dioxane, 1,2-dimethoxyethane and 1,2-diethoxyethane; and ketones such as acetone, methyl ethyl ketone, methyl isobutyl ketone, diethyl ketone and cyclohexanone.

The reaction temperature ranges from 20° C. to the boiling point of a solvent to be used. The reaction is usually completed in several tens of minutes to several tens of hours.

After completion of the reaction in each step mentioned above, isolation and purification may be performed according to standard procedures for synthetic organic chemistry to give a target product. Alternatively, the resulting reaction mixture may be directly provided for the subsequent reaction without any treatment.

The structure of a target product can be determined, e.g., by measuring various spectra including $^1$H-NMR, IR and MASS spectra.

Preferred examples of the thus obtained compound of Formula (3) will be specifically shown below.

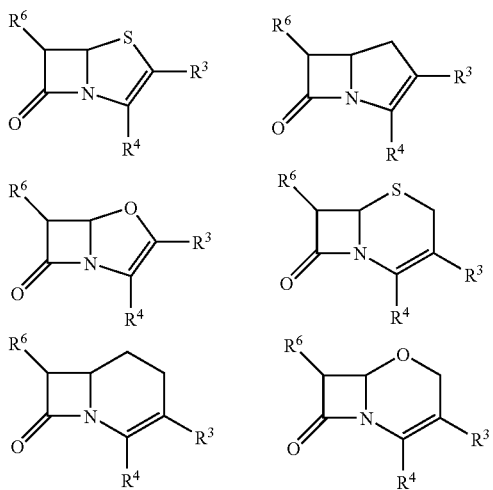

(wherein $R^3$, $R^4$ and $R^6$ are as defined above.)

These compounds are each useful as a starting material for the production of β-lactam antibacterial agents (see, e.g., JP 63-162694 A, U.S. Pat. No. 4,448,732, JP 2000-302787 A, etc.).

EXAMPLES

The present invention will now be further described in more detail in the following examples, which are not intended to limit the scope of the invention. Without departing from the spirit of the invention, changes and modifications can be made to the compounds of Formulae (1) to (3) as well as the type of solvents and bases to be used.

In the example and the comparative example shown below, the starting material (3S,4R)-1-(allyloxy)oxoacetyl-3-((R)-1-t-butyldimethylsilyloxyethyl)-4-(2-tetrahydro-furanyl) carbonylthio-azetidin-2-one is a known substance (see, e.g., JP 63-162694 A).

Example 1

Preparation of allyl (5R,6S)-6((R)-1-t-butyldimethyl-silyloxyethyl)-7-oxo-3-((R)-2-tetrahydrofuryl)-4-thia-1-azabicyclo[3.2.0]hept-2-ene-2-carboxylate (3-2)

(Step A) Preparation of (3S,4R)-1-(allyloxycarbonyl)-triethoxyphosphanylidenemethyl-3-((R)-1-t-butyldimethyl-silyloxyethyl)-4-((R)-2-tetrahydro-furanyl)carbonylthio-azetidin-2-one (2-2)

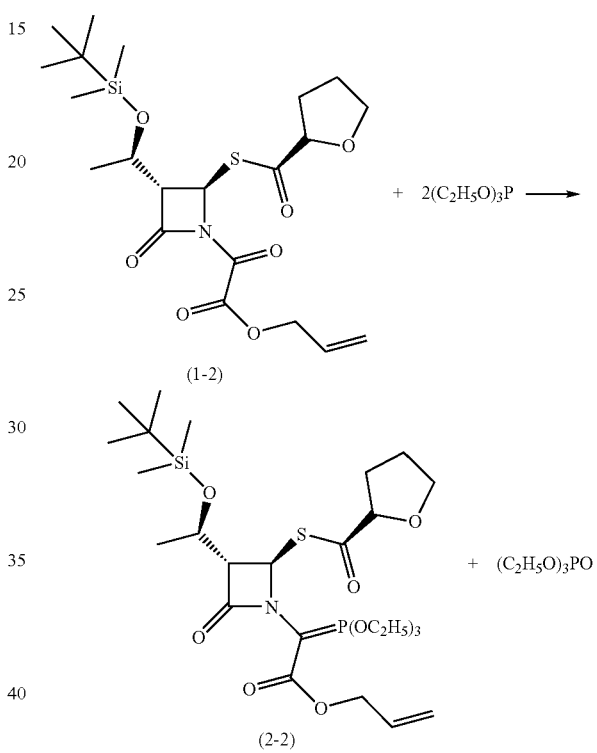

Triethyl phosphite (99.7 g, 0.6 mol) was charged into a 500 ml four-necked flask equipped with a thermometer, a stirring machine and a rectifying column. (3S,4R)-1-(Allyloxy) oxoacetyl-3-((R)-1-t-butyldimethylsilyloxyethyl)-4-((R)-2-tetrahydrofuranyl)carbonylthio-azetidin-2-one (1-2) (70.7 g, 0.15 mol) was melted at 70° C. and slowly added dropwise to the flask at 20° C. to 40° C. while stirring. After completion of the dropwise addition, the mixture was stirred for an additional 1.5 hours. The reaction mixture heated up to around 80° C.

A part of the reaction mixture was sampled and analyzed by high performance liquid chromatography (HPLC) to confirm the complete disappearance of the starting compound (1-2).

(Step B) Removal of Triethyl Phosphite

The reaction mixture was then heated in a vacuum to remove triethyl phosphate. Removal of triethyl phosphite was performed as follows. The internal pressure of the reaction vessel was set between 0.7 to 1.3 kPa and the reaction mixture was heated at 50° C. to 70° C. (150 minutes) to distill off most part of triethyl phosphate, followed by heating under conditions of 0.7 kPa and 75° C. to 80° C. (65 minutes).

A part of the reaction mixture was sampled and analyzed by gas chromatography (GC) under the following conditions to determine whether triethyl phosphite was removed from the reaction mixture, indicating that the content of triethyl phosphite was below the detection limit.

The yield of the reaction mixture was 114.6 g.

(GC Conditions)

Gas chromatography: Shimadzu GC-8A TCD
Column: 20% silicone DC-550 on Celite 545 60/80 Mesh 3 mm ϕ×2 m
Column temperature: 100° C. to 170° C. (increase at 5° C./min)
Injection/detector temperature: 190° C.
Carrier gas: He 1.0 kg/cm$^2$
Current: 100 mA
Sensitivity: 1 mV
Injection volume: 2 μL (Step C) Cyclization of (3S,4R)-1-(allyloxycarbonyl)-triethoxyphosphanylidenemethyl-3-((R)-1-t-butyldimethyl-silyloxyethyl)-4-((R)-2-tetrahydrofuranyl)carbonylthio-azetidin-2-one (2-2)

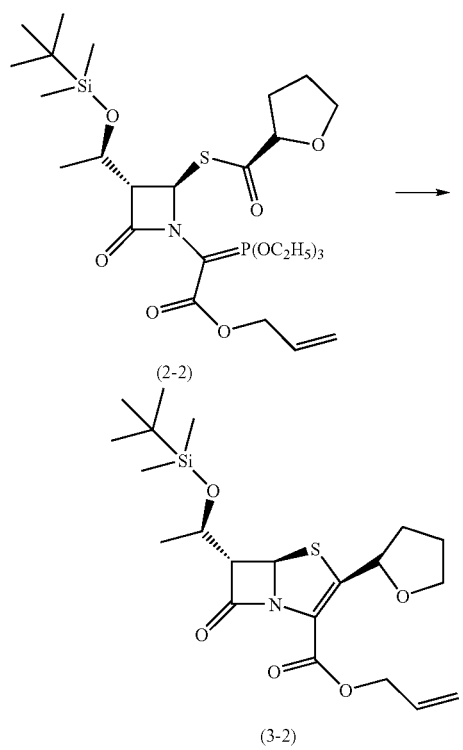

The reaction mixture obtained in Step B above was dissolved in methyl isobutyl ketone (300 ml) and the resulting solution was heated at reflux for 8 hours. The reaction mixture was evaporated in a vacuum to remove methyl isobutyl ketone, thereby giving a mixture (120.1 g) containing a target product and triethyl phosphate ((C$_2$H$_5$O)$_3$PO). This mixture was analyzed by high performance liquid chromatography, indicating that the target compound (3-2) was obtained in 93% yield over three steps A to C.

Comparative Example 1

The same procedure as shown in Example 1 was repeated, except that the reaction mixture obtained in Step B of Example 1 was evaporated at 1.3 kPa and at an internal temperature of 50° C. to 70° C. (215 minutes) to remove triethyl phosphite. Gas chromatography analysis was performed under the same conditions as used in Example 1, indicating that 5% by weight of triethyl phosphate remained in the reaction mixture to be provided for Step C.

Cyclization was then performed under the same conditions as used in Example 1.

The resulting reaction product was analyzed by high performance liquid chromatography, indicating that the target compound (3-2) was obtained in only 84% yield over three steps A to C. Gas chromatography analysis indicated that structurally unidentified products were generated in substantial amounts.

INDUSTRIAL APPLICABILITY

As explained above, according to the present invention, the yield of cyclization can be significantly improved when conventional processes simply include an additional simple step for removal of trialkyl phosphate from the reaction mixture, which step involves heating the reaction mixture at a given temperature in an increased vacuum.

The invention claimed is:

1. A method for preparing a cyclic compound of Formula (3-1),

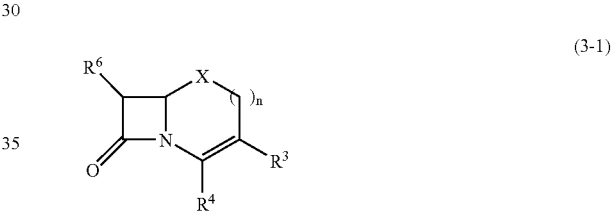

wherein X represents CH2, O or S, n represents 0 or 1, R$^3$ represents an alkyl group containing 1 to 6 carbon atoms, an alkenyl group containing 1 to 6 carbon atoms, a phenyl group, a heterocyclic group or a heteroylmethyl group, R$^4$ represents an alkoxycarbonyl group containing 1 to 6 carbon atoms, a haloalkoxycarbonyl group containing 1 to 6 carbon atoms or an alkenyloxycarbonyl group containing 1 to 6 carbon atoms, and R$^6$ represents a hydroxyalkyl group whose hydroxy moiety is protected with a protecting group, which comprises the following steps:

a step of reacting a compound of Formula (1-1),

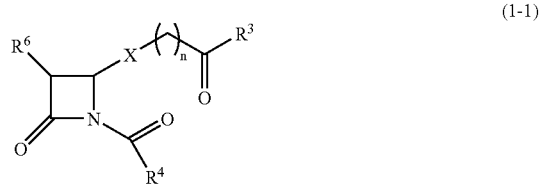

wherein X, n, R$^3$, R$^4$ and R$^6$ are as defined above, with a triethyl phosphite in an amount of 2 to 5 moles per mole of the compound to obtain a reaction mixture containing a compound of Formula (2-1),

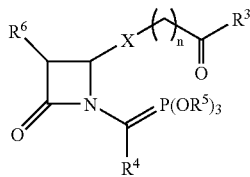

(2-1)

wherein X, n, $R^3$, $R^4$ and $R^6$ are as defined above; and $R^5$ is ethyl;

a step of removing unreacted triethyl phosphite from the reaction mixture including reducing the internal pressure of the vessel holding the reaction mixture to 0.7 kPa or below and heating the vessel at 75° C. to 80° C. to distill off the triethyl phosphite remaining in the reaction mixture; and a step of heating the resulting mixture in a diluent.

2. The method for preparing a cyclic compound according to claim 1, wherein the step of removing unreacted trialkyl phosphite from the reaction mixture comprises reducing the internal pressure of the vessel holding the reaction mixture to 0.7 to 2 kPa and heating the vessel at 50° C. to 75° C. to distill off low-boiling products, followed by reducing the internal pressure of the vessel to 0.7 kPa or below and heating at 75° C. to 80° C. to distill off the trialkyl phosphite remaining in the reaction mixture.

* * * * *

UNITED STATES PATENT AND TRADEMARK OFFICE
CERTIFICATE OF CORRECTION

PATENT NO.        : 7,459,551 B2                                    Page 1 of 1
APPLICATION NO.   : 10/508659
DATED             : December 2, 2008
INVENTOR(S)       : Akira Kaneko It is certified that error appears in the above-identified patent and that said Letters Patent is hereby corrected as shown below:

On the title page, Item 73, the Assignees information is incorrect. Item 73 should read as follows:

-- (73) Assignees: Nippon Soda Co., Ltd., Tokyo (JP);
                    Asubio Pharma Co., Ltd., Tokyo (JP) --

Signed and Sealed this
Twenty-sixth Day of November, 2013

Margaret A. Focarino
*Commissioner for Patents of the United States Patent and Trademark Office*